(12) United States Patent
Mastorakis

(10) Patent No.: US 6,913,595 B2
(45) Date of Patent: Jul. 5, 2005

(54) MEDICAL DEVICE AND LOCKING MECHANISM THEREFOR

(75) Inventor: Emmanuel Mastorakis, Fribourg (CH)

(73) Assignee: Nicodel S.A., Fribourg (CH)

( * ) Notice: Subject to any disclaimer, the term of this patent is extended or adjusted under 35 U.S.C. 154(b) by 24 days.

(21) Appl. No.: 10/069,688

(22) PCT Filed: Jan. 25, 2001

(86) PCT No.: PCT/EP01/00817

§ 371 (c)(1),
(2), (4) Date: Jul. 15, 2002

(87) PCT Pub. No.: WO02/26295

PCT Pub. Date: Apr. 4, 2002

(65) Prior Publication Data

US 2002/0173751 A1 Nov. 21, 2002

(30) Foreign Application Priority Data

Dec. 22, 2000 (GR) ........................................ 20000100459

(51) Int. Cl.[7] ............................. A61M 5/00; A61M 5/32
(52) U.S. Cl. ........................ 604/110; 604/192; 128/919
(58) Field of Search ........................... 604/93.01, 110, 604/111, 181, 187, 192, 195, 197, 198, 218, 220, 228; 128/919

(56) References Cited

U.S. PATENT DOCUMENTS

| 4,675,005 A | 6/1987 | DeLuccia |
| 4,747,830 A | 5/1988 | Gloyer et al. |
| 4,904,242 A | 2/1990 | Kulli |
| 4,950,241 A | 8/1990 | Ranford |
| 5,047,016 A | 9/1991 | Dolgin et al. |
| 5,084,029 A | 1/1992 | Nacci nēTagliaferri et al. |
| 5,163,918 A | 11/1992 | Righi et al. |
| 5,201,718 A | 4/1993 | Whisson |

(Continued)

FOREIGN PATENT DOCUMENTS

| EP | 321903 A2 | 6/1989 |
| EP | 467173 A1 | 1/1992 |
| EP | 500613 B1 | 9/1992 |
| EP | 602882 B1 | 6/1994 |
| EP | 636381 B1 | 2/1995 |
| FR | 2718358 | 10/1995 |
| GB | 2306332 | 5/1997 |
| GB | 2315022 | 1/1998 |
| GB | 2342047 | 4/2000 |
| IT | 1264806 | 10/1996 |
| IT | 1269480 | 4/1997 |
| WO | WO9007948 | 7/1990 |
| WO | WO9108788 | 6/1991 |
| WO | WO9112842 | 9/1991 |
| WO | WO9211883 | 7/1992 |
| WO | WO9962579 | 12/1999 |

Primary Examiner—Nicholas D. Lucchesi
Assistant Examiner—Mark K. Han
(74) Attorney, Agent, or Firm—Price, Heneveld, Cooper & DeWitt & Litton

(57) ABSTRACT

A locking mechanism 10 for a medical sharp device such as a syringe assembly 62 includes a retainer part 12 for retaining a hypodermic needle 22, and a connector part 14. The retainer part includes lugs 46 for engagement with a recess 82 formed in a neck 70 of the syringe assembly. When a plunger 72 of the syringe assembly is pushed fully forwards, the lugs 56 of the retainer part 12 engage behind a ledge 54 of the connector part 14 and the lugs 46 disengage from the recess 82. The plunger 72 may then be retracted, pulling the needle 22 into the barrel 64 of the assembly. The neck portion may be eccentrically mounted on the barrel and means 116,118 may be provided for preventing rotation of the plunger 72 in the barrel 64.

60 Claims, 6 Drawing Sheets

U.S. PATENT DOCUMENTS

| | | | |
|---|---|---|---|
| 5,342,309 A | * 8/1994 | Hausser | 604/110 |
| 5,344,403 A | 9/1994 | Lee | |
| 5,364,359 A | 11/1994 | van den Haak | |
| 5,378,240 A | 1/1995 | Curie et al. | |
| 5,395,346 A | 3/1995 | Maggioni | |
| 5,399,170 A | 3/1995 | Whitley | |
| 5,405,326 A | 4/1995 | Haber et al. | |
| 5,415,638 A | 5/1995 | Novacek et al. | |
| 5,415,646 A | 5/1995 | Roth | |
| 5,415,648 A | 5/1995 | Malay et al. | |
| 5,417,661 A | 5/1995 | Stringer et al. | |
| 5,431,631 A | 7/1995 | Lu | |
| 5,462,531 A | 10/1995 | Novacek et al. | |
| 5,496,278 A | 3/1996 | Buff | |
| 5,514,100 A | 5/1996 | Mahurkar | |
| 5,531,705 A | 7/1996 | Alter et al. | |
| 5,538,507 A | 7/1996 | De Kler et al. | |
| 5,569,203 A | 10/1996 | Chen | |
| 5,584,817 A | 12/1996 | van den Haak | |
| 5,593,387 A | 1/1997 | Rupp | |
| 5,613,952 A | 3/1997 | Pressly, Sr. et al. | |
| 5,667,494 A | 9/1997 | van den Haak | |
| 5,685,862 A | 11/1997 | Mahurkar | |
| 5,688,240 A | 11/1997 | Novacek et al. | |
| 5,720,727 A | 2/1998 | Alexander et al. | |
| 5,762,633 A | 6/1998 | Whisson | |
| 5,785,687 A | 7/1998 | Saito | |
| 5,788,672 A | 8/1998 | Saito | |
| 5,792,107 A | 8/1998 | Petrocelli | |
| 5,879,339 A | 3/1999 | Saito | |
| 5,891,092 A | 4/1999 | Castellano | |
| 5,891,105 A | 4/1999 | Mahurkar | |
| 5,931,813 A | 8/1999 | Liu | |
| 5,938,641 A | 8/1999 | Villanueva | |
| 5,968,020 A | 10/1999 | Saito | |
| 5,976,108 A | 11/1999 | Liu | |
| 5,997,511 A | 12/1999 | Curie et al. | |
| 6,210,371 B1 | * 4/2001 | Shaw | 604/164.08 |
| 2001/0021821 A1 | 9/2001 | Wang et al. | |

* cited by examiner

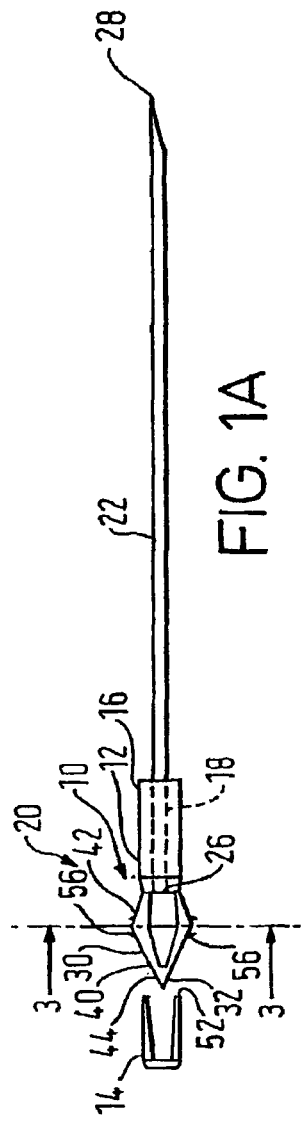
FIG. 1A
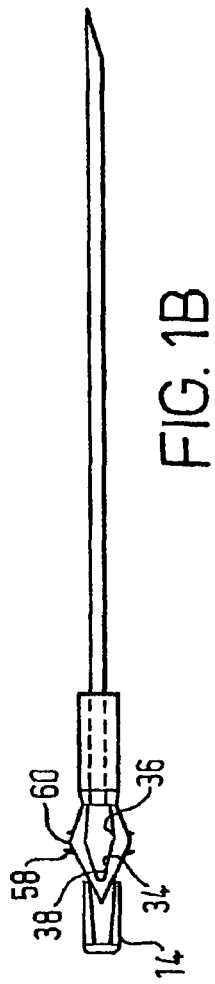
FIG. 1B
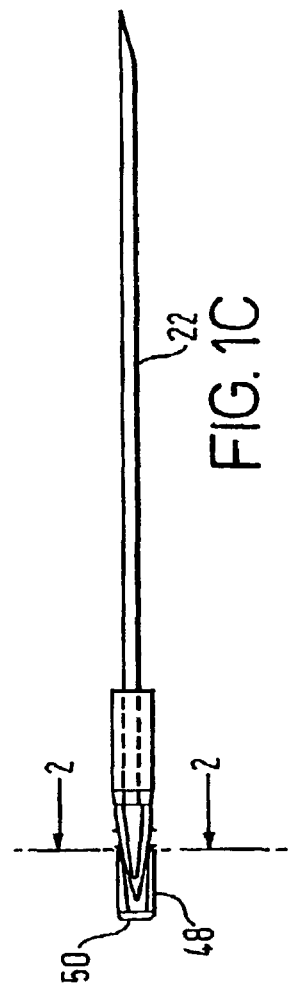
FIG. 1C
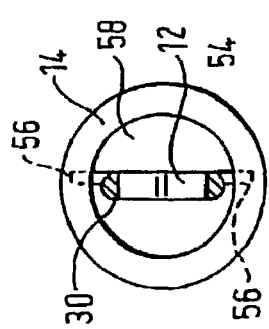
FIG. 2
FIG. 3

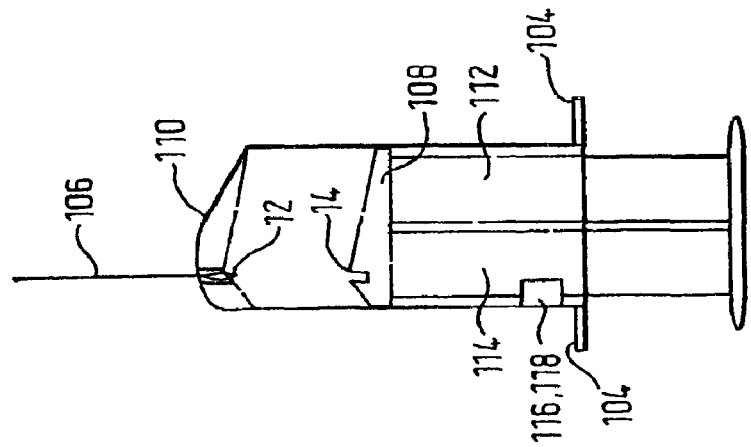
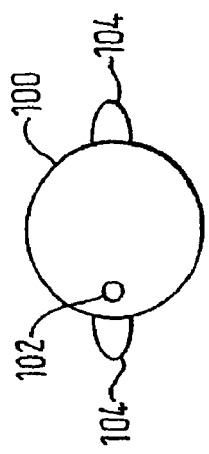
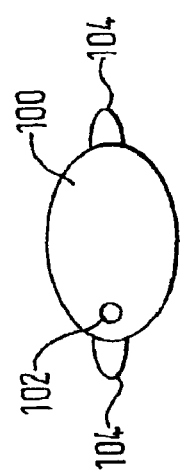
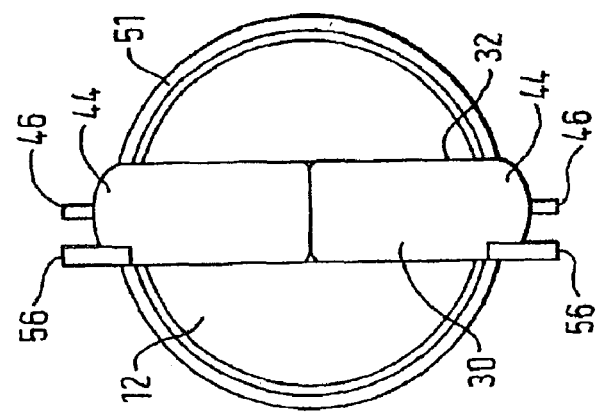

MEDICAL DEVICE AND LOCKING MECHANISM THEREFOR

The present invention relates to locking mechanisms for controlling engagement between parts moveable relative to one another in medical sharp devices. The invention also relates to medical devices, such as hypodermic needle devices including syringe assemblies, cannulas and catheters including butterfly catheters, which incorporate such mechanisms. The invention also relates to hypodermic needle assemblies.

There is a need for non-reusable safe medical sharp devices such as hypodermic syringes. It is known that the reuse of hypodermic needle devices is unsafe practice. There is a risk to patients and others of infection. The improper disposal of used syringes and needles also presents a risk to healthcare workers and others. It is also known that needle-stick incidents are undesirable for both healthcare workers and patients since infections such as HIV, Hepatitis B and C, Ebola fever, Lassa fever, Syphilis, Tuberculosis, Herpes, Brucellosis and Streptococcal conditions may be accidentally transmitted during needlestick incidents.

Furthermore, it is now believed that the BSE and/or vCJD protein or proteins may be resistant to sterilisation processes such that the problems and dangers of reuse of human medicine sharp devices are also applicable in veterinary medicine.

Some attempts have been made to address the above problems by providing what are known as "safety" syringes which are supposed to be non-usable once they have been used once. One type of known "safety" syringe includes a spring which is adapted to force a hypodermic needle backwards into a retracted position inside a barrel of a hypodermic syringe. A problem with this type of apparatus is that the spring can cause the hypodermic needle to spring back suddenly out of the patient, causing discomfort to the patient especially when the operator of the device is applying a slight bending moment to the needle at the time of the sudden needle retraction by the spring. Furthermore, the spring can be very expensive, since the steel used can be required by medical standards to remain sterile for a number of years and thus very expensive steel must be employed.

Another type of known "safety" syringe include an outer barrel which is sprung forwards by a spring along the main syringe barrel and over the needle once a plunger of the syringe has been depressed. The mechanism is very complicated and expensive due to the need for the spring and additional sheath barrel.

Another type of known "safety" syringe, as described in U.S. Pat. No. 5,431,631, includes a mushroom-shaped locking device for locking the front of a hypodermic needle assembly's plunger to a needle retainer once the plunger has been fully depressed. The plunger may then be manually retracted, overcoming the rather complicated engagement at a forward location between a bead on the retainer part and the barrel. This arrangement is not only complicated and expensive incorporating a number of parts, but the patient may feel an uncomfortable sensation as the mushroom-shaped part suddenly engages. Furthermore, the needle is spaced a substantial distance in front of the end of plunger movement along the barrel meaning that, when the device is used for injection purposes, substantial volume of the material to be injected is wasted.

Known types of "safety" syringe are very expensive being up to ten times more costly than "standard" syringes of the reusable type. Although the use of reusable syringes is mandatory in some jurisdictions, the cost of known "safety" syringes is such that it is proving difficult to comply with this mandatory requirement.

Known hypodermic needle assemblies use glue to retain and seal the steel needle of the assembly in a retainer part therefor. The use of glue is somewhat unreliable and has a cost implication.

Furthermore, in known systems it is often not possible to change needles before use of an assembly. In cases in which this is possible, there is often a substantial non-displaced volume of fluid in front of a plunger of the device when the plunger is fully depressed and this means that a substantial amount of fluid is wasted when using the device for injection purposes.

The present invention aims to alleviate at least some of the problems of the prior art.

According to a first aspect of the present invention there is provided a locking mechanism as set out in claim 1. This locking mechanism is highly advantageous since it is very simple and can be incorporated in a cost-effective manner into various types of medical device, such as hypodermic syringes for injection or extraction of material from patients in a cost-effective manner. Furthermore, in preferred embodiments of the invention, the locking mechanism can be incorporated to allow one actuation of the device, followed by retraction of the medical sharp device. The medical sharp device will normally comprise a needle, but may comprise other types of sharp device, such as a knife or other cutting instrument.

A number of preferred features of the locking mechanism will now be described.

The first formation may comprise a lug and the second formation may comprise a recess or cavity formed in the body. A pair of said lugs may be provided on opposite sides of the retainer part and the recess may comprise an annular recess in the body part.

Preferably, the retainer part includes a flexible leg, the first formation being located on the leg, the connector part being adapted to flex the leg on engagement with the retainer part to move the first formation relative to the body part. Most preferably, the said retainer part includes at least two said legs, the connector part being adapted to move the said legs towards one another on engagement with the retainer part. Therefore, before engagement of the retainer part by the connector part, the legs may be outwardly biased for engagement with the body part for holding the retainer part firmly relative to the body part, but on engagement of the retainer part by the connector part, the connector part may move the said legs for reducing the effectiveness of engagement between the retainer part and the body part, and the connector part may then be moved for disengaging the retainer part from the body part.

The connector part may be linearly moveable to engage the retainer part, the connector part, on engagement with the retainer part, causing movement of at least one said leg in a direction generally perpendicular to the said direction of movement of the connector part.

The said legs may be mutually joined at respective ends thereof. Preferably, the legs form a diamond shape when their respective ends are joined. Accordingly, the structure formed by the legs may be relatively resilient, such that, when the legs are engaged with the body part, the engagement is relatively effective.

The body part may take various forms but will usually be an item fixed to or part of a main body of the medical device. Thus the body part may comprise, for example, a central tubular body part of a catheter e.g. a butterfly catheter or cannula, or may comprise a portion of a barrel part of a hypodermic needle assembly, such as a neck portion of such an assembly, especially when the barrel comprises a main cylindrical part joined at a front end thereof by a tapered or conical shoulder to a neck.

The body part may comprise an element releasably coupled to a main body of a medical device, for example, a releasable needle retention hub in the case of a hypodermic needle assembly.

Preferably, each said leg has an inner surface and an outer surface, the outer surface being longer than the inner surface. It is believed that this construction has the advantage that the leg will be relatively resilient against bending in response to engagement thereof by the connector part. The inner surface of the leg may be relatively flat and the outer surface may be curved or outwardly convex, in order to provide the longer configuration of the outer surface relative to the inner surface.

The connector part preferably comprises a generally cylindrical element. The connector part may include an internal bore into which at least part of the retainer part is insertable. The connector part preferably includes an annular ledge at an entrance to the bore. The retainer part preferably includes at least one connector protrusion for engagement behind the annular ledge. Preferably, two said connector protrusions are provided, the connector protrusions being asymmetrically configured for asymmetrically configured for asymmetrically engaging the annular ledge. Thus, the engagement between the connector protrusions and the annular ledge may be such that the connector part provides a tilting force on the retainer part, and this may be highly beneficial when the retainer part is used to retain a hypodermic needle, so that in preferred embodiments the needle may be retracted inside a barrel of a hypodermic syringe and then automatically tilted by the locking mechanism, e.g. so that it cannot be reused.

In a preferred embodiment, the retainer part is adapted to retain a hypodermic needle, the retainer part including an elongate bore passing therethrough, the bore being engageable with a cylindrical outer surface of a needle. Preferably, the elongate bore includes internal ribs, such as circumferentially extending ribs, for sealingly gripping a needle, for example, with a push-fit and/or interference fit. Accordingly, it is not necessary to use glue to mount the needle.

Accordingly, according to a second aspect of the present invention there is provided a hypodermic needle assembly as set out in claim 23. The substantial advantage of a push fit sealing engagement between the needle and the retainer for the needle is that glue is not needed. The push-fit may alternatively or additionally comprise an interference fit (e.g. a push interference fit or a shrink interference fit in which the retainer part is shrunk on to the needle. Therefore, the unreliability and cost of using glue may be avoided.

The bore preferably includes a series of ribs for sealingly engaging an outer surface of the needle. The ribs are preferably circumferentially extending ribs. This has the advantage that the needle is gripped at a number of locations spaced axially therealong, and the series of ribs provide a series of sealing engagements between the needle and retainer such that the sealing between the needle and retainer is relatively effective.

A further aspect of the invention provides a hypodermic needle assembly as set out in claim 26. Various optional features are mentioned in claims 27 to 36.

A further aspect of the invention provides a medical device as set out in claim 37.

A further aspect of the invention provides a medical device as set out in claim 38. Preferably, the device comprises a hypodermic needle device. The device may comprise a catheter (e.g. a butterfly catheter) or cannula or other hypodermic needle device. The medical device may comprise a hypodermic syringe. In this case, the retainer part may be adapted to retain a hypodermic needle of the device and the connector part may be mounted on a plunger of the syringe. The hypodermic syringe may be used for injecting or extracting material such as fluid to or from a patient.

Preferably, the syringe includes a barrel, the barrel having a main cylindrical part, a conical or tapered shoulder portion at a forward end of the main cylindrical part, and a neck portion in front of the shoulder portion, the said second formation of the locking mechanism being formed internally in the neck portion of the barrel. Preferably, the neck portion of the barrel includes a front end and a rear end thereof, the rear end being adjacent a front end of the shoulder portion, the second formation of the locking mechanism comprising an annular internal recess or cavity formed at the rear end of the neck portion. It will therefore be appreciated that an advantage of the location of the second formation at the rear end of the neck portion is that the hypodermic needle may be located at least partially inside the neck portion with the adjacent end of the hypodermic needle located inside the neck portion and preferably no more than 25% or 50% of the way along the neck portion from the rear end thereof, such that, when used for injecting fluid, a small amount of fluid/material will be wasted.

Preferably, the device includes a hub part for releasably sealably retaining the retainer part on the barrel of the syringe. Thus, the retainer part and needle may be removed from the device and replaced, such as with a retainer and needle of different configuration, such as when a different needle diameter or gauge is required. The hub may include a stop surface for preventing forward movement of the retainer part relative to the barrel. Thus, when the plunger is pushed forwards, the hub maintains the retainer part and needle in position, but once the connector part has engaged the retainer part and altered the engagement between the retainer part and the body part, e.g. the preferred annular recess in the neck portion of the barrel, the plunger may be retracted such that the connector part may pull the retainer part and needle into the barrel. The plunger preferably includes a weak region, such that after use, the plunger may, if desired, be snapped to assist in preventing further use of the device. Furthermore, the plunger preferably includes a jam mechanism for preventing removal of the used hypodermic needle from the barrel.

A further aspect of the invention provides a locking mechanism for a medical device comprising a retainer part for retaining medical sharp devices, the retainer part including at least one connector portion thereof adapted for engagement against a body part of a medical sharp device, and a connector part, the connector part being adapted for movement to engage the connector portion for connection therewith, movement of the connector part once connected to the connector portion causing movement of the retainer part.

Preferably, the connector portion comprising a flexible leg.

Preferably, two said flexible legs are provided extending generally parallel to one another, engagement of the connector part with the legs causing the legs to move towards one another.

Preferably, the legs are joined together in a diamond shape preferably having a general V-shaped end portion joined to an inwardly tapering portion adjacent a needle retaining body of the retainer.

Preferably, each said leg includes a lug adapted for engagement with a recess formed in the body part, the movement of the connector part to engage the leg causing a reduction in the force of engagement between the lug and recess.

Preferably, the connector part includes a generally cylindrical bore, the bore being adapted to receive each said leg on engagement of the connector part therewith.

Preferably, the bore includes an annular ledge at an entrance thereto and each said leg includes a connector projection adapted to ride over and lock past the ledge on insertion into the bore.

Another aspect of the invention is set out in claim 53. Various optional features are mentioned in claims 54 to 56.

The present invention may be carried out in various ways and a preferred embodiment of a locking mechanism and its incorporation in a preferred hypodermic syringe assembly and preferred butterfly catheter in accordance with the invention will now be described by way of example with reference to the accompanying drawings, in which:

FIGS. 1A to 1C are various schematic side views of a preferred embodiment of a locking mechanism in accordance with the present invention, a preferred retainer part thereof retaining a hypodermic needle;

FIG. 2 is a schematic sectional view in the direction 2 shown in FIG. 1C;

FIG. 3 is a schematic sectional view in the direction 3 shown in FIG. 1A;

FIG. 9 is a view corresponding to FIG. 8, in the direction "9" in FIG. 8 but excluding the connector part 14;

FIG. 10 is an end view of an embodiment of a syringe assembly having an eccentrically located neck portion;

FIG. 11 is a further embodiment of a hypodermic needle assembly, in which the section of a barrel of the assembly is non-circular; and FIG. 12 is a schematic side view of each of the assemblies shown in FIGS. 10 and 11.

Figure 4A:
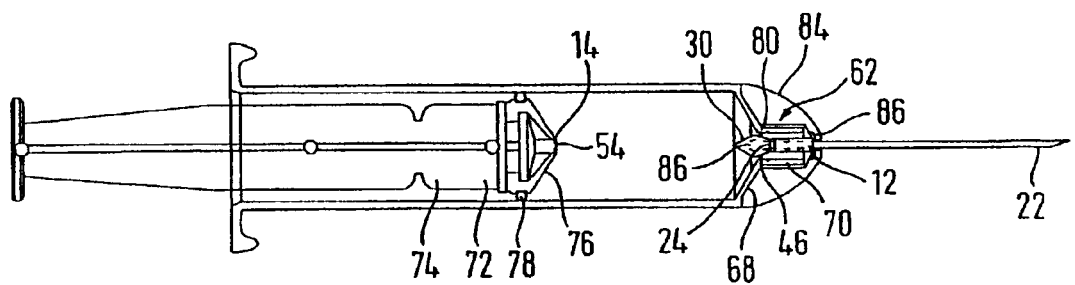
FIGS. 4A to 4F are schematic side views showing the operation of the preferred locking mechanism of FIGS. 1A to 1C and 2 and 4, incorporated in a preferred hypodermic needle assembly.

A preferred locking mechanism 10 in accordance with a preferred embodiment of the present invention is shown in FIGS. 1A to 1C, FIG. 2 and FIG. 3. The locking mechanism 10 comprises a retainer part 12 and a connector part 14. The retainer part 12 includes a body part 16 or a generally cylindrical needle retainer 16 having an elongate bore 18 formed therethrough. An adjacent end 20 of a hypodermic needle 22 has a circular entrance aperture 24 thereto flush with one end 26 of the bore 18. The other, distal end 28 of the needle 22 is sharp, and it will be understood that the needle 22 has an internal bore (or lumen) (not shown) formed therealong for the transmission of material, such as medicine being injected to, or blood or other bodily fluids being extracted from a patient.

The retainer part 12 includes a pair of resilient legs 30 formed integrally with the cylindrical needle retainer 16, the legs 30 being mutually joined at one end 32 thereof. The legs 32 form a diamond-shaped section, consisting of V-shape end portion 31 adjacent an inwardly tapered portion 33 adjacent the needle retainer 16. The joining of the legs in a "V" provides additional resilience against squashing thereof by the connector part 14 as will be described below. Furthermore, each leg 30 includes a generally flat inner surface 34, formed by two flat surfaces 36,38 and a generally concave or curved outer surface 40, formed by two surfaces 42,44. The arrangement of flat 34,36,38 surfaces and concave/curved 40,42,44 surfaces, provides additional resilience for the legs 30 against movement towards one another.

Figure 7:
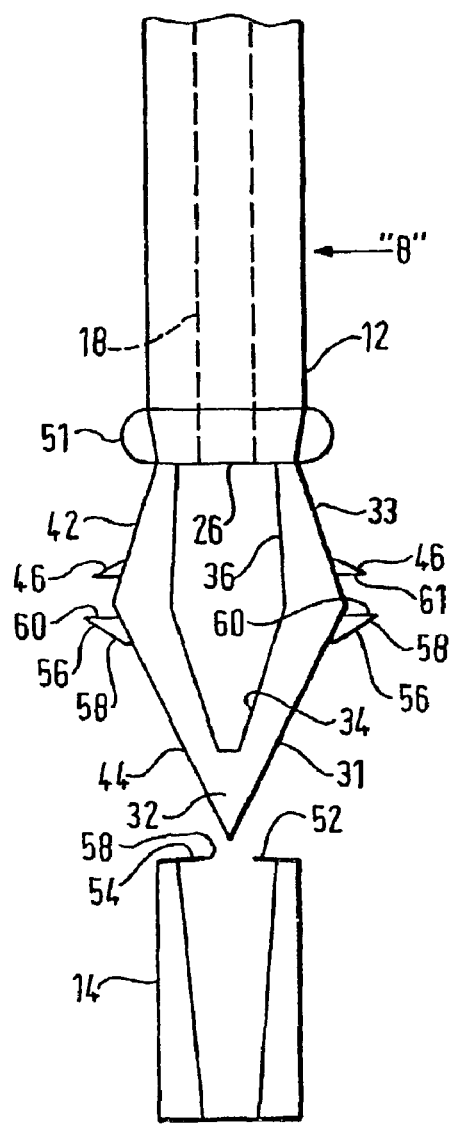
FIG. 7 is an enlarged side view of the retainer part and connector part shown in FIGS. 1 to 4.
Figure 8:
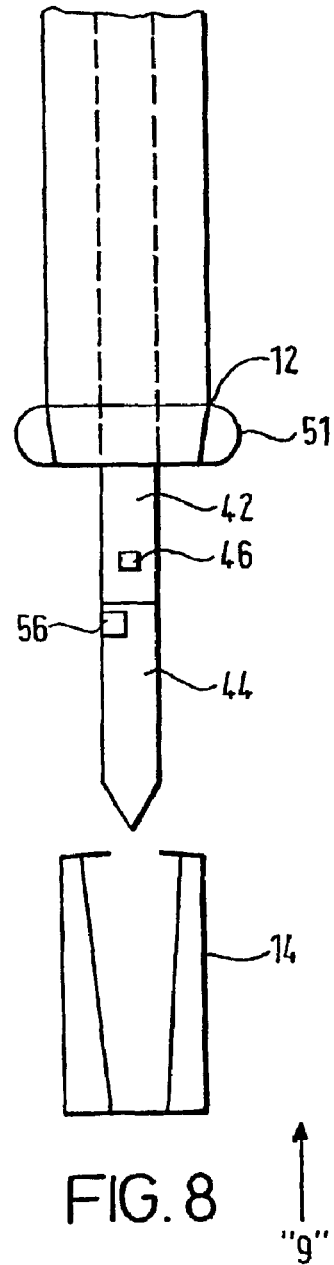
FIG. 8 is a view corresponding to FIG. 7, in the direction of the arrow marked 8 in FIG. 7.

FIGS. 7 to 9 show enlarged views of the retainer 12 and connector 14. It will be appreciated that the connector 14 is cylindrical and FIGS. 7 and 8 thus show a schematic section through this part.

As shown in FIG. 3, each leg 30 includes a formation 46 formed thereon in the form of a lug 46 extending generally transverse to the longitudinal direction of the needle 22.

As shown in FIGS. 4B and 7 to 9 the retainer 12 may include an annular seal 51 formed adjacent a rear end thereof (omitted for clarity in other drawings) for sealing inside the neck of the syringe. This seal is located well inside the neck portion as is the rear entrance to the needle and this means that almost no fluid is wasted as excess when injecting.

The seal 51 may be replaced with alternative sealing means in other embodiments The connector part 14 of the locking mechanism comprises a cup-shaped element 48 having one end 50 which may be closed (or in other embodiments open) and a second end 52 which is open but includes an annular ledge 54 which is inwardly extending at an entrance to the cup. The legs 30, in addition to the lugs 46 (which are symmetrically located about the longitudinal axis of the hypodermic needle), includes two further lugs 56 which are located somewhat asymmetrically about the axis of the needle 22. The further lugs 56 are spaced further along the legs 30 from the needle retainer part 16 of the retainer part 12 than the lugs 46.

As shown in the sequence of FIGS. 1A to 1C, the connector part 14 may be moved linearly towards the retainer part 12 until the inner edge 58 of the ledge 54 engages the legs 30 as shown in FIG. 1B. Further movement of the connector part 14 linearly in the axial longitudinal direction of the needle 22 causes the legs 30 to be transversely moved towards one another. Eventually, the ledge 54 rides over the further lugs 56, the further lugs 56 having chamfered surfaces 58 allowing the ledge 54 to ride over the lugs 56, but transverse flat surfaces 60 (perpendicular to the needle axis) opposing the chamfered surfaces 58, the flat transverse surfaces 60 thus preventing removal of the connector part 14 from the retainer part 12, once the ledge 54 has ridden over the lugs 56 to place the connector part 14 and retainer part 12 in the engaged configuration shown in FIG. 1C.

Thus, as shown in FIGS. 4A to 4F, the preferred locking mechanism 10 may be incorporated in a preferred syringe assembly 62 in accordance with a preferred embodiment of the present invention.

As best shown in FIGS. 4A to 4F, the needle 22 is a push-fit in the needle retainer 16, the needle retainer including a series of circumferential ribs on the internal bore 18 thereof, e.g. about ten spaced circumferentially extending ribs, the ribs 18 compressing against the needle 22 in order to hold the needle 22 in position and provide a good seal. Accordingly, it is not necessary to use glue to attach the needle 22.

The syringe assembly 62 includes a barrel 64 having a main cylindrical part 66, a conical shoulder 68 and a cylindrical neck 72. The assembly 62 also has a plunger 72 having a stem 74 for operating a piston 76, the piston 76 being sealed against the barrel main cylindrical part 66 with an O ring 78. The neck 70 of the barrel 64 includes at a rear end 80 thereof an internal annular recess or cavity 82. The retainer part 12 holding the needle 22 may be connected to a hub 84 (or the alternative hub 84 shown in FIG. 5) and, later, the retainer part 12 may be pushed into the neck 70 of the barrel 64 to the configuration shown in FIG. 4A in which the lugs 46 are resiliently engaged in the internal annular recess 82 at the rear end 80 of the neck 70. The resilience of the lugs 46 and the legs 30 is such that when the plunger 72 is drawn backwards to draw material such as a vaccine, medicine or bodily material such as blood into the barrel 64, the retainer part 12 and hypodermic needle 22 are retained in position, with transverse surfaces 61 of lugs 46 engaging in the recess 82. Furthermore, the hub 84 is provided with a stop element/stop surface 86 for preventing forward movement of the needle 22 when the plunger 72 is pushed forwards. It will be appreciated that there is a gap 86 between the legs 30 such that fluid may flow from the barrel, through the gap 86 into the entrance aperture 24 and along the needle 22 or, of course, in the opposite direction.

Figure 4B:
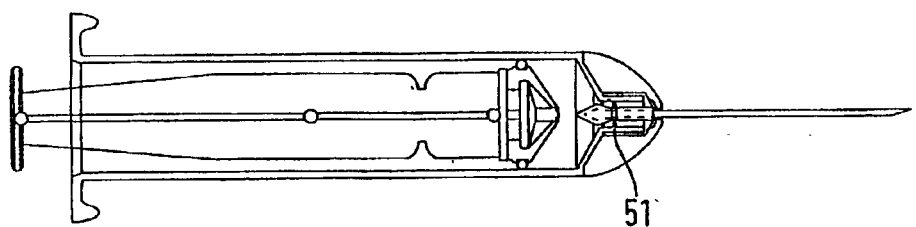
Figure 4C:
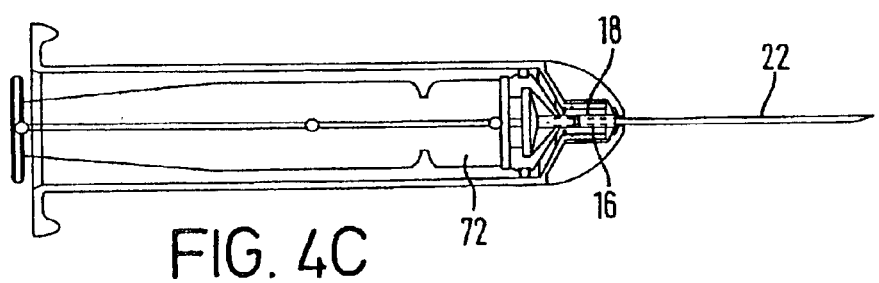
Figure 4D:
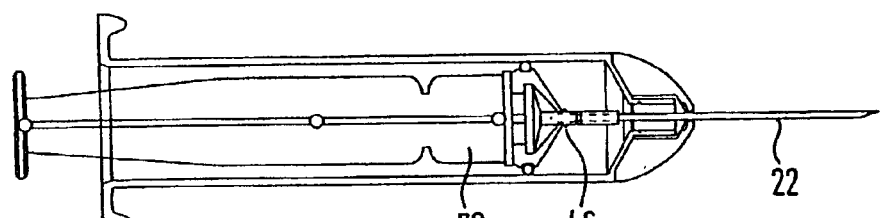
Figure 4E:
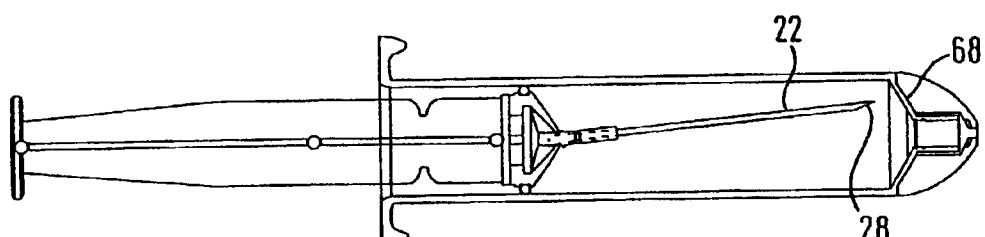
Figure 4F:
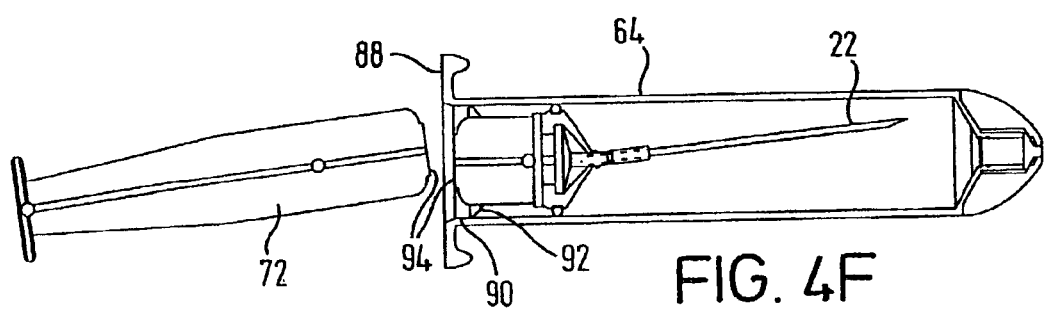
Figure 5:
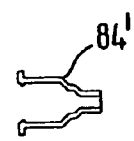
FIG. 5 shows a schematic side view of an alternate hub for the assembly of FIGS. 4A to 4F.
Figure 6A:
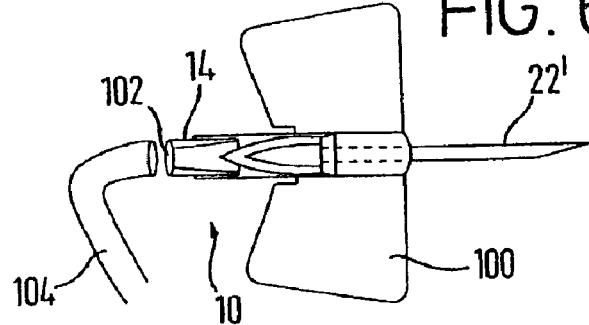
FIGS. 6A to 6D show various schematic side views of the locking mechanism of FIGS. 1A to 1C when incorporated in a preferred butterfly catheter having a slightly shorter needle than the needle shown in FIGS. 1A to 1C.
Figure 6B:
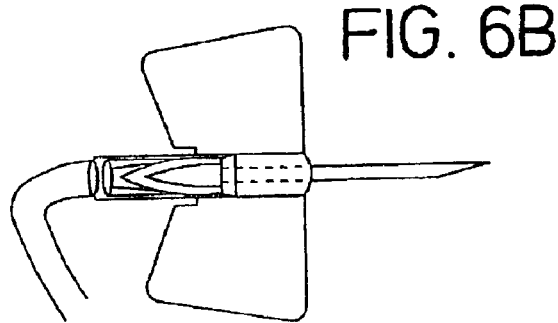
Figure 6C:
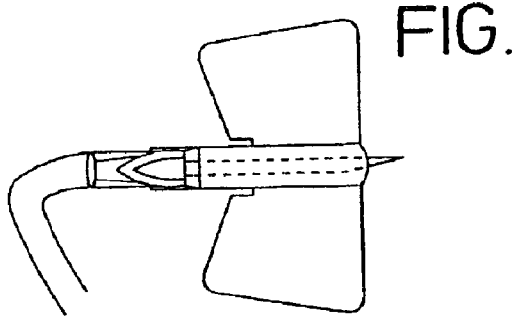
Figure 6D:
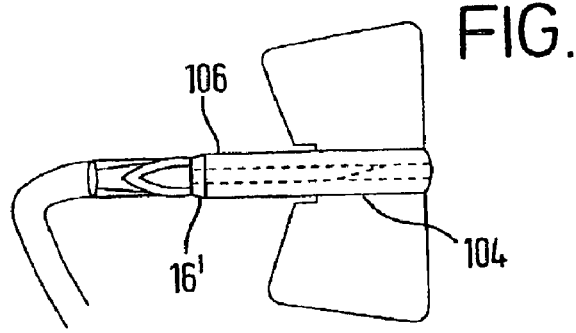

When the syringe assembly 62 is used to give an injection, the plunger is pushed forwards, for example, from the position shown in FIG. 4A to the position shown in FIG. 4B and then to the position shown in FIG. 4C. As the plunger 72 approaches the configuration shown in FIG. 4C, it will be appreciated that the locking mechanism 10 adopts first the configuration shown in FIG. 1A, then the configuration shown in FIG. 1B and then the configuration shown in FIG. 1C which is the same as the configuration shown in FIG. 4C. As the connector part 14 of the locking mechanism 10 moves along the legs 30, it squashes the legs 30 towards one another and, in doing so, the lugs 46 disengage from the internal annular recess 82 in the neck portion 70 of the barrel 64 and, the ledge 54 of the connector part 14 rides over the lugs 56. Accordingly, when the plunger 72 is pulled backwards to the position shown in FIG. 4B, the connector part 14 pulls the retainer part 12 and needle 22 with it. The needle 22 maintains a generally longitudinally configuration until the end 28 passes through the neck portion 70 and along the inside of the shoulder 68 of the barrel. Due to the thin flat nature of the legs 30 and the asymmetric configuration of the lugs 56, together with the inward squashing forces provided to the legs 30 by the ledge 54, the connector part 14 provides a tilting force on the retainer part 12 and needle 22, such that the needle tilts by about 5° as shown in FIG. 4E and FIG. 4F, such that it is then not possible to push the needle forwards out through the neck 70 for reuse. Furthermore, the rear end 88 of the barrel 64 includes a slight constriction 90 and the stem 74 includes a jamming element 92 shown for the purposes of clarity schematically only and only in FIG. 4F, which prevents the stem 74 from being fully removed from the barrel 64. Thus, not only is the needle 22 safely enclosed in the barrel 64 after use, but the needle 22 also cannot be removed for attempted reuse on another apparatus. As indicated in FIG. 4F, a weak spot 94 on the stem 74 of the plunger 72 conveniently allows the plunger to be snapped for showing even the most inexperienced user or persistent attempted reuser of needles 22 that the needle 22 has been used and is now inoperative and should not be reused.

FIGS. 6A to 6D show a development on the apparatus shown in FIGS. 4A to 4F in which the preferred locking mechanism 10 of FIGS. 1A to 1C, 2 and 3 is instead incorporated in a butterfly catheter 100, this apparatus including a shorter needle 22. The locking mechanism 10 works on a similar principle in FIGS. 6A to 6D and the connector part 14 has an open end 102 which may be connected to a fluid tube 104 for various purposes such as provision of a drip (not shown). After use, the needle 22 may be retracted into the butterfly device body 104 and a slightly shorter needle retainer 16 of the retainer part 12 and the retainer 16 shown in FIGS. 1 to 4 may be pulled longitudinally behind a tube section 106 of the body 104 such that the needle retainer 16 cannot be pushed inside the tube 106 again and the needle 22 therefore cannot be pushed forwards out of the body 104 for reuse.

The embodiments of the invention, it is envisaged, may have application in the fields of both human and veterinary medicine.

It will be appreciated from the above that embodiments of the invention may provide a hypodermic medical device such as a syringe assembly in which a needle is secured, without glue or adhesive, in its optimal position for use in injecting or extracting. The needle may be subsequently locked into the inner end of a plunger or piston to permit withdrawal wholly into the barrel of the syringe or the body of the device. The complete assembly may then be discarded without fear of accidental infection through needlestick. The device/syringe is thus rendered safe and cannot be refilled or reused and it can be disposed of safely. The device may be produced in quantity at a competitive price. The retainer part 12 which may also be considered a central hub combines a central channel for transmission of fluid being injected or extracted with a ribbed internal contour that engages with the surface of the needle. This internal locking mechanism shows that the needle is firmly secured in a base that is in turn married with forward end or neck of the syringe barrel. The outer surface of the central hub or retainer part is contoured such that the combined central hubs/retainer and needle assembly can be easily and firmly attached to the neck of the syringe barrel readying the syringe ready for use. The syringe may then be filled in the normal way for injection by drawing back the plunger, thus drawing injectable fluid into the barrel. The union of the needle hub and barrel of course forms an effective seal to prevent leakage and appropriate sealing means (not shown) are of course provided for that purpose. Once the injection is complete, and with the plunger fully depressed, the piston engages the lugs 56 on the hubs that shut the hub together with the needle can be drawn back into the barrel of the syringe. Due to the asymmetric nature of the lugs 56 and the resilience of the legs and connector part, the needle tip 28 is displaced through about 5° as it is pulled back so that it is no longer in line with the aperture at the neck of the barrel and this prevents re-extension of the needle and reuse of the syringe. With the needle fully withdrawn into the barrel the whole assembly can be discarded. Subject to local procedures, e.g. of a medical centre in which the device is used, it may be permissible for the unit to be consigned to general waste rather than a sharps bin requiring special handling and disposal.

In the case of fluid extraction from the body, e.g. of blood, the plunger may be depressed to a point short of where the lugs 56 engage with the connector part 12, and the plunger may then be retracted as fluid is drawn in. When the fluid is transferred into a vial (not shown) or other receptacle (not shown) the plunger will be fully depressed such that it engages with the lugs. Accordingly, when the plunger is pulled back again, the needle is withdrawn into the barrel of the syringe and the unit can be discarded.

In devices such as catheters or butterflies which are in turn connected to a drip or other equipment for the purpose of e.g. administering fluids into the body, the locking of the needle is secured by pulling the tail-end of the device until the needle disappears into the device.

Further advantages of preferred embodiments of the present invention will be apparent in that needles may be interchanged before use so that the clinician or other user can match a selection of needles with a selection of barrels. Thus, a standard barrel may be capable of taking a range of needle sizes and profiles, while larger or smaller barrels may be supplied for applications falling outside the most commonly used sizes. Accordingly, the system is very flexible. Sometimes, there is a requirement when preparing an injection for a first needle to draw the fluid from a vial and another to perform the injection using the same barrel. Of course, the preferred embodiments of the present invention are able to meet this requirement.

It is envisaged that blood collection (phlebotomy) may be used with embodiments of the invention, thus making "self-blunting" needles unnecessary.

Due to the removability of the needles in preferred embodiments of the invention, it is possible to keep barrels and needles apart before use. This gives flexibility and choice to e.g. the clinician who also has security and cost-saving implications since stores of syringes are readily targeted and robbed by drug users and medical personnel may also be targeted for theft. Accordingly, the ability to keep needles separately from barrels can reduce the risk of problems.

Another advantage is that preferred embodiments of the invention may allow a plunger and safety needle to be fitted to a prefilled container, subject to dimensions, with a secure seal between the barrel and needle mounting. This is important since some prefilled syringes such as glass syringes for Meningitis immunisation do not always have in the prior art a needle which sits tightly in the neck of the barrel and fluid leaks out. A further particular advantage is that devices such as hypodermic needles in accordance with preferred embodiments of the present invention may be simple to use compared to other safety syringes and may be priced at a level affordable to health services and workers in most countries since the cost may be similar to that of standard, i.e. basic reusable products.

The connector part 14 may be adapted such that in other embodiments, once the connector part is engaged with the retainer part, the full length of the legs 30 is located inside the connector part such that there is no passage for fluid past the connector part along the needle and the needle cannot therefore be used again to suck fluid into the barrel.

Hubs 84 for needles of different sizes may be colour-coded to provide helpful information.

The syringe assembly 62 is preferably rubber-free, including the O ring 78. Instead of using a push-on hub 84 as shown in FIGS. 4A to 4F for a syringe assembly 62 (it will be appreciated that the hub 84 snap-locks onto the front of the barrel in a conventional way), a half-turn/screw-lock may be implemented for the engagement of the hub 84 with the barrel 64, this generally being considered the American connection method, whereas the traditional conical snap connection system is used more in Europe.

The barrel of the syringe assembly 62 may be made from various materials including medical grade polypropylene. Alternatively, a clear polycarbonate may be used. Other materials may be used. Once assembled, the medical device/syringe assembly may be sterilised, for example, using ethylene oxide or gamma rays or an electron beam method. The plunger may be made from various materials including polyurethane or other suitable materials and the plunger may be coloured, for example red or yellow or other suitable colours. The retainer part and connector part of the locking mechanism are preferably formed in plastics material and the needle is most preferably steel, being rolled, welded, cut and polished in a conventional way.

FIG. 10 shows a modification of the assembly shown in FIG. 4. The syringe barrel 100 in this embodiment has an eccentrically located forward neck portion 102, as shown in FIG. 10, which also shows finger tabs 104 of the assembly. As shown in FIG. 12, the needle 106 is retained by a retainer 12 the same as that shown in FIGS. 8 to 10 and the plunger 108 has a connector part 104 located in an eccentric position corresponding to the position of the neck 102 and needle 106, the connector part 14 being as shown and described with reference to the embodiments of FIGS. 1 to 4 and 7 to 9. The assembly in FIGS. 10 and 12 includes an eccentrically domed hub 110. The plunger 108 has a stem 112 with an X-shaped section. One arm 114 of the stem 112 runs in a groove 116 defined by two grooved plates 118, only one of which is shown in FIG. 12, the plates preventing rotation of the plunger and stem. FIG. 11 shows an alternative embodiment similar to the embodiment of FIG. 10, but the barrel 100 of the syringe assembly has a non-circular section, namely an elliptical section. In this embodiment, the groove and plates 116,118 may be omitted. It will be appreciated that the side view of the FIG. 11 embodiment is shown in FIG. 12, as is the side view of the FIG. 10 embodiment. In both of these embodiments, the needle 106 is retained in place by lugs 46 on an internal recess of the syringe, and, once fully depressed, the connector part 14 on the plunger 108 engages with the retainer part 12, and the needle 106 is then retracted inside the syringe assembly, on retraction of the plunger 108.

The use of a medical device such as a syringe assembly having an eccentric neck portion may be desirable in cases in which the cross-dimension or diameter of the assembly is relatively large. The eccentric location of the neck portion may enable a user of the assembly to place the assembly relatively close to or relatively parallel to a body surface of a patient, for example, for inserting a needle at a shallow angle into a patient.

In the syringe assemblies of FIG. 4 and FIGS. 10 to 12, an important advantage is that the retainer 12 and needle 22 may be compatible with various syringe plunger devices or other devices and/or that the neck of the syringe may be connected to various types of device such as a needle with hub or a tube for pushing or sucking fluid along the tube. Thus, one type of locking mechanism/needle may be applicable to various devices, thus reducing costs. For example, the same locking mechanism, i.e. retainer part 12 and connector part 14 may be used in 1, 5, 10, 20 ml or other sizes of hypodermic syringe assembly. Instead of using the bubble or dome-shaped hub 84 shown in FIGS. 4A to 4F and the eccentric bubble or dome-shaped hub shown in FIG. 12, a standard hub like the hub 84' may be employed.

Devices in accordance with the invention may have application in either human medical or veterinary fields and may even have application outside medical fields.

Various modifications may be made to the embodiments shown without departing from the scope of the invention as defined by the claims as interpreted under Patent Law.

What is claimed is:

1. A locking mechanism for controlling engagement between parts movable relative to one another in medical sharp devices, the mechanism comprising: a retainer part for retaining a medical sharp, the retainer part having a first formation which is engageable with a second formation located on a body part of a medical sharp device and a connector part which is movable relative to the body part to a position in which the connector part and retainer part are in a mutually engaged configuration, wherein the connector part, during movement to the engaged configuration, is adapted to alter the relative engagement between the first and second formations to enable release of the retainer part from the body part, the retainer part including two flexible legs, each leg having a said first formation located thereon, the connector part being adapted to flex the legs, on engagement with the retainer part, to move the legs towards one another, the legs being mutually joined at respective distal ends thereof before movement of the connector part to the engaged configuration, the legs being arranged to disengage from the body part when moving toward one another.

2. A locking mechanism as claimed in claim 1 in which the first formation and second formation comprise a lug and a recess, each being formed on or in one of the retainer part and the body part.

3. A locking mechanism as claimed in claim 2 in which a pair of said lugs are provided on opposite sides of the retainer part and in which the recess comprises an internal annular recess in the body part.

4. A locking mechanism as claimed in claim 1 in which the legs form a diamond shape.

5. A locking mechanism as claimed in claim 1 in which each leg has an inner surface and an outer surface, the outer surface being longer than the inner surface.

6. A locking mechanism as claimed in claim 5 in which the inner surface is relatively flat and the outer surface is outwardly concave or relatively curved compared to the inner surface.

7. A locking mechanism as claimed in claim 1 in which the connector part includes a bore into which at least part of the retainer part is insertable.

8. A locking mechanism as claimed in claim 7 in which the bore includes an annular ledge at an entrance thereto, and in which the retainer part includes at least one connector protrusion for engagement behind the annular ledge.

9. A locking mechanism as claimed in claim 8 in which two said connector protrusions are provided, the connector protrusions being adapted to engage the annular ledge asymmetrically.

10. A locking mechanism as claimed in claim 9 in which each connector protrusion has a chamfered surface for riding over the annular ledge and an opposing step surface for engagement behind the ledge.

11. A locking mechanism as claimed in claim 1 in which the retainer part is adapted to retain a hypodermic needle, the retainer part including an elongate bore passing therethrough, the bore being engageable with a cylindrical outer surface of a needle.

12. A locking mechanism as claimed in claim 11 in which the elongate bore includes internal ribs for sealingly gripping a needle.

13. A medical device including a locking mechanism as claimed in claim 1.

14. A medical device as claimed in claim 13 which comprises a hypodermic needle device.

15. A medical device as claimed in claim 14 which comprises a butterfly.

16. A medical device as claimed in claim 14 which comprises a catheter.

17. A medical device as claimed in claim 14 which comprises a hypodermic syringe and in which the retainer part is adapted to retain a hypodermic needle of the device and the connector part is mounted on a plunger of the syringe.

18. A medical device as claimed in claim 17 in which the syringe includes a barrel, a conical shoulder portion at a forward end of a main cylindrical part of the barrel and a neck portion in front of the shoulder portion, the said second formation of the locking mechanism being formed internally in the neck portion.

19. A medical device as claimed in claim 18 in which the neck portion of the barrel includes a front end and a rear end, the rear end being adjacent a front end of the shoulder portion, the second formation comprising an annular internal recess formed at the rear end of the neck portion.

20. A medical device as claimed in claim 13 in which the retainer part is removably mounted on the body part of the device.

21. A medical device as claimed in claim 20 in which the retainer part is removably mounted on the body part of the device, and which includes a hub part for releasably sealably retaining the retainer part on the barrel of the syringe.

22. A medical device as claimed in claim 21 in which the hub includes a stop surface for preventing forward movement of the retainer part relative to the barrel.

23. A locking mechanism as claimed in claim 1 in which the distal ends of the legs are joined together as a V-shaped end portion.

24. A locking mechanism for a medical device comprising a retainer part for retaining medical sharp devices, the retainer part including at least one connector portion thereof adapted for engagement against a body part of a medical sharp device, and a connector part, the connector part being adapted for movement to engage the connector portion for connection therewith, movement of the connector part once connected to the connector portion causing movement of the retainer part, the connector portion comprising two flexible legs, the connector part being adapted to flex the legs, on engagement with the connector portion, to move the legs towards one another, the legs being mutually joined at respective distal ends thereof before movement of the connector part to the engaged configuration, the legs being arranged to disengage from the body part when moving toward one another.

25. A locking mechanism as claimed in claim 24 in which the legs are joined together in a diamond shape.

26. A locking mechanism as claimed in claim 24 in which each said leg includes a formation adapted for engagement with a recess formed in the body part.

27. A locking mechanism as claimed in claim 24 in which the connector part includes a generally cylindrically bore, the bore being adapted to receive each said leg on engagement of the connector part therewith.

28. A locking mechanism as claimed in claim 27 in which the bore includes an annular ledge at an entrance thereto and each said leg includes a connector projection adapted to ride over the lock past the ledge on insertion to the bore.

29. A medical device including a needle assembly as claimed in claim 24.

30. A locking mechanism as claimed in claim 24 in which the distal ends of the legs are joined together as a V-shaped end portion.

31. A locking mechanism for controlling engagement between parts movable relative to one another in medical sharp devices, the mechanism comprising: a retainer part for retaining a medical sharp, the retainer part having a first formation which is engageable with a second formation located on a body part of a medical sharp device and a connector part which is movable relative to the body part to a position in which the connector part and retainer part are in a mutually engaged configuration, wherein the connector part, during movement to the engaged configuration, is adapted to alter the relative engagement between the first and second formations to enable release of the retainer part from the body part, the retainer part including two flexible legs, each leg having a said first formation located thereon, the connector part being adapted to flex the legs, on engagement with the retainer part, to move the legs towards one another, the legs being integrally formed with the respective distal ends thereof being mutually joined together, the legs being arranged to disengage from the body part when moving toward one another.

32. A locking mechanism as claimed in claim 31 in which the first formation and second formation comprise a lug and a recess, each being formed on or in one of the retainer part and the body part.

33. A locking mechanism as claimed in claim 32 in which a pair of said lugs are provided on opposite sides of the retainer part and in which the recess comprises an internal annular recess in the body part.

34. A locking mechanism as claimed in claim 31 in which the legs form a diamond shape.

35. A locking mechanism as claimed in claim 31 in which each leg has an inner surface and an outer surface, the outer surface being longer than the inner surface.

36. A locking mechanism as claimed in claim 35 in which the inner surface is relatively flat and the outer surface is outwardly concave or relatively curved compared to the inner surface.

37. A locking mechanism as claimed in claim 31 in which the connector part includes a bore into which at least part of the retainer part is insertable.

38. A locking mechanism as claimed in claim 37 in which the bore includes an annular ledge at an entrance thereto, and in which the retainer part includes at least one connector protrusion for engagement behind the annular ledge.

39. A locking mechanism as claimed in claim 38 in which two said connector protrusions are provided, the connector protrusions being adapted to engage the annular ledge asymmetrically.

40. A locking mechanism as claimed in claim 39 in which each connector protrusion has a chamfered surface for riding over the annular ledge and an opposing step surface for engagement behind the ledge.

41. A locking mechanism as claimed in claim 31 in which the retainer part is adapted to retain a hypodermic needle, the retainer part including an elongate bore passing therethrough, the bore being engageable with a cylindrical outer surface of a needle.

42. A locking mechanism as claimed in claim 41 in which the elongate bore includes internal ribs for sealingly gripping a needle.

43. A locking mechanism for a medical device comprising a retainer part for retaining medical sharp devices, the retainer part including at least one connector portion thereof adapted for engagement against a body part of a medical sharp device, and a connector part, the connector part being adapted for movement to engage the connector portion for connection therewith, movement of the connector part once connected to the connector portion causing movement of the retainer part, the connector portion comprising two flexible legs, the connector part being adapted to flex the legs, on engagement with the connector portion, to move the legs towards one another, the legs being integrally formed with the respective distal ends thereof being mutually joined together, the legs being arranged to disengage from the body part when moving toward one another.

44. A locking mechanism as claimed in claim 43 in which the legs are joined together in a diamond shape.

45. A locking mechanism as claimed in claim 43 in which each said leg includes a formation adapted for engagement with a recess formed in the body part.

46. A locking mechanism as claimed in claim 43 in which the connector part includes a generally cylindrically bore, the bore being adapted to receive each said leg on engagement of the connector part therewith.

47. A locking mechanism as claimed in claim 46 in which the bore includes an annular ledge at an entrance thereto and each said leg includes a connector projection adapted to ride over the lock past the ledge on insertion to the bore.

48. A medical device including a needle assembly as claimed in claim 43.

49. A medical device including a locking mechanism as claimed in claim 43.

50. A medical device as claimed in claim 49 which comprises a hypodermic needle device.

51. A medical device as claimed in claim 50 which comprises a butterfly.

52. A medical device as claimed in claim 50 which comprises a hypodermic syringe and in which the retainer part is adapted to retain a hypodermic needle of the device and the connector part is mounted on a plunger of the syringe.

53. A medical device as claimed in claim 52 in which the syringe includes a barrel, a conical shoulder portion at a forward end of a main cylindrical part of the barrel and a neck portion in front of the shoulder portion, the said second formation of the locking mechanism being formed internally in the neck portion.

54. A medical device as claimed in claim 53 in which the neck portion of the barrel includes a front end and a rear end, the rear end being adjacent a front end of the shoulder portion, the second formation comprising an annular internal recess formed at the rear end of the neck portion.

55. A medical device as claimed in claim 49 which comprises a catheter.

56. A medical device as claimed in claim 49 in which the retainer part is removably mounted on the body part of the device.

57. A medical device as claimed in claim 56 in which the retainer part is removably mounted on the body part of the device, and which includes a hub part for releasably sealably retaining the retainer part on the barrel of the syringe.

58. A medical device as claimed in claim 57 in which the hub includes a stop surface for preventing forward movement of the retainer part relative to the barrel.

59. A locking mechanism as claimed in claim 43 in which the distal ends of the legs are joined together as a V-shaped end portion.

60. A locking mechanism as claimed in claim 43 in which the distal ends of the legs are joined together as a V-shaped end portion.

* * * * *